United States Patent [19]

Lüders

[11] Patent Number: 4,866,165

[45] Date of Patent: Sep. 12, 1989

[54] PROCESS FOR THE PREPARATION OF ALKYLOLIGOGLYCOSIDES

[75] Inventor: Harald Lüders, Recklinghausen, Fed. Rep. of Germany

[73] Assignee: Hüls Aktiengesellschaft, Marl, Fed. Rep. of Germany

[21] Appl. No.: 16,135

[22] Filed: Feb. 18, 1987

[30] Foreign Application Priority Data

Jun. 12, 1986 [DE] Fed. Rep. of Germany ....... 3619796

[51] Int. Cl.[4] ......................... C07H 1/00; C07G 3/00; C08B 37/00

[52] U.S. Cl. .................................... 536/18.6; 536/4.1; 536/18.5; 536/124

[58] Field of Search ..................... 536/18.5, 18.6, 124, 536/4.1

[56] References Cited

U.S. PATENT DOCUMENTS

| | | | |
|---|---|---|---|
| 3,707,535 | 12/1972 | Lew | 536/18.6 |
| 3,839,318 | 10/1974 | Mansfield | 536/18.6 |
| 3,974,138 | 8/1976 | Lew | 536/18.6 |
| 4,223,129 | 9/1980 | Roth et al. | 536/120 |
| 4,349,669 | 9/1982 | Klahr et al. | 536/124 |
| 4,393,203 | 7/1983 | Mao et al. | 536/124 |
| 4,510,306 | 4/1985 | Langdon | 536/124 |
| 4,557,729 | 12/1985 | McDaniel, Jr. et al. | 8/111 |
| 4,683,297 | 7/1987 | Yanami et al. | 536/18.6 |
| 4,704,453 | 11/1987 | Lorenz et al. | 536/124 |

*Primary Examiner*—Ronald W. Griffin
*Assistant Examiner*—Nancy S. Carson
*Attorney, Agent, or Firm*—Oblon, Spivak, McClelland, Maier & Neustadt

[57] ABSTRACT

Alkyloligoglycosides are prepared by glycoside alcoholysis of lower alkylglycosides with alcohols. The average degree of oligomerization is adjusted by the use of catalytic amounts of an acid.

8 Claims, No Drawings

PROCESS FOR THE PREPARATION OF ALKYLOLIGOGLYCOSIDES

BACKGROUND OF THE INVENTION

1. Field of the Invention

The invention relates to a method of preparing alkyloligoglycosides by glycoside alcoholysis of lower alkylglycosides with alcohols.

2. Discussion of the Background

Alkyloligoglycosides can be prepared entirely or partly based on renewable raw materials. These compounds command great interest because of their low toxicity, their very good biological degradability, and their interesting practical properties. According to F. A. Hughes and B. W. Lew, J.A.O.C.S. 47 (1970), 162, the properties of the alkyloligoglycosides are strongly determined by their degree of oligomerization. For this reason there is interest in processes by which alkyloligoglycosides with definite average degrees of oligomerization can be selectively prepared.

Glucose can be converted smoothly to an alkylglucoside by the Fischer glycoside synthesis with hydrophilic alcohols such as methanol or ethanol and acid catalysis. With hydrophobic alcohols, on the other hand, solubility problems occur.

According to U.S. Pat. No. 3,219,656, higher alkylglucosides are obtained by first preparing butylglucoside, which is then subjected to alcoholysis with a higher alcohol. This process requires large amounts of cation exchanger, however.

German OS No. 19 43 689 discloses that higher alkyloligosaccharides can be prepared from butylglucoside by transacetalization with alcohols containing 11 to 32 carbon atoms and acid catalysis. The degree of oligomerization is inversely proportional to the moles of alcohol used per mole of butylglucoside.

This reciprocal relationship is also confirmed in German No. OS 19 05 523. The alcohol-monosaccharide molar ratios in the transacetalization in this case are set at 0.05 to 12, whereby alkyloligoglucosides are obtained with an average of 25 to 1.4 glucose units per molecule.

Accordingly, the alcohol-carbohydrate ratios chosen for high degrees of oligomerization must be so low that the course of the reaction is not impaired by the formation of viscous products. With low degrees of oligomerization, on the other hand, the process is carried out with very large excesses of alcohol that must be distilled off after completion of the reaction. Because of the very diverse amounts of alcohol which are required, a continuous method of production suitable for products having varying degrees of oligomerization from 1.5 to 5, for example, in a single system can only be realized at great expense.

According to U.S. Pat. No. 3,839,318 and 4,465,828, the acid added as catalyst affects only the rate of reaction. No effect of the catalyst concentration on the degree of oligomerization is disclosed. Further, this effect is not expected since it was stated in U.S. Pat. No. 4,223,129 that the catalyst concentration has no effect on the degree of oligomerization in the preparation of methyloligoglycosides.

A need exists therefore for a method of preparing alkyloligoglycosides which is easily adjusted and which reproducibly produces specific degrees of oligomerization.

SUMMARY OF THE INVENTION

Accordingly, one object of the present invention is to produce a process for the preparation of alkyloligoglycosides which is easily adjusted for varying degrees of oligomerization.

Another object of the present invention is to provide a process for the preparation of alkyloligoglycosides which reproducibly produces specific degrees of oligomerization.

A further object of the invention is to provide a method of preparing alkyloligoglycosides having alkyl groups containing up to 24 carbon atoms and in which the reaction mixtures are easily stirrable.

Still another object of the invention is to provide a process for the preparation of alkyloligoglycosides which does not use large excesses of alcohol.

These objects and other objects of the present invention which will become apparent from the following specification have been achieved by the process for the preparation of alkyloligoglycosides of the present invention, comprising the steps of:

contacting an alkylglycoside, alkyloligoglycoside or mixture thereof with an alcohol in the presence of an acid, wherein said alcohol has at least three carbon atoms more than the alkyl groups of said alkylglycoside or alkyloligoglycoside, and regulating the degree of oligomerization of said alkyloligoglycoside by adjusting the effective acid concentration.

DETAILED DESCRIPTION OF THE PREFERRED EMBODIMENTS

Alkylglycosides, alkyloligoglycosides, or mixtures of these are used as starting materials for the qlycoside alcoholysis. They may contain monosaccharides such as glucose, mannose, galactose, fructose, ribose, or xylose. Glucose derivatives, alkylglucosides, and alkyloligoglucosides, are preferably used. The alkyl portion of the starting materials contains at least 3 carbon atoms fewer than the alcohol used. The alkyl portion preferably has from 2 to 6 carbon atoms. Especially preferred starting materials ar n-butylglucoside, n-butyloligoglucosides, and mixtures of these.

These products are obtained, for example, in the acid-catalyzed alcoholysis of starch or starch hydrolyzates. The alkylglycosides and alkyloligoglycosides can be used in pure form or mixed with the alcohol that was used for their preparation.

Primary alcohols with 4 to 24 carbon atoms are used as the second component for the glycoside alcoholysis. The alcohols preferably contain from 8 to 20 carbon atoms. Examples of these are natural surface-active alcohols or fatty alcohols such as those formed by the hydrogenation of fatty acids and fatty acid derivatives, among other methods, and also fully synthetic Ziegler alcohols and oxoalcohols. Mixtures of alcohols can also be used. The alcohols can have branches in the carbon chain. However, linear alcohols are preferably used.

The glycoside alcoholysis is catalyzed by acids. The acid added serves at the same time to regulate the degree of oligomerization. In general, approximately 2 to 200 milliequivalents of acid are needed per kg of alcohol. Strong mineral acids or organic sulfonic acids are used, with sulfuric acid being preferred.

There may be acid present already in the starting material. The effective acid concentration is therefore adjusted either by appropriate addition of measured amounts of acid or by partial neutralization of acid that is present Alcohol and alkylglycoside or alkyloligoglycoside are used in molar ratios of 10 : 1 to 0.5 : 1 (calculated as moles of alcohol per mole of saccharide unit) for the glycoside alcoholysis. The molar ratios are preferably 5 : 1 to 1 : 1.

The short chain alcohols liberated during the glycoside alcoholysis and possibly present in addition to the starting material are removed from the reaction mixture by distillation. It is desirable for the boiling point of the short chain alcohol to be more than 30° C. below the boiling point of the alcohol used for the glycoside alcoholysis.

The short chain alcohol is distilled off at a reaction temperature of 80° to 140° C. If necessary, vacuum can also be applied. An inert gas can also be bubbled through the melt.

After completion of the glycoside alcoholysis, the acid is neutralized by an alkali. Excessive alcohol is then distilled under vacuum. Temperatures in excess of 150° C. should be avoided because of the risk of decomposition of the product.

The process has the following advantages: (1) The preparation of alkyloligoglycosides with various average degrees of oligomerization can be carried out with a constant alcohol/carbohydrate ratio of starting materials. Thus, with a lauryl alcohol/nbutylglucoside molar ratio of 1.7 : 1, for example, the amount of sulfuric acid can be increased from 13 to 80 milliequivalents per kg of lauryl alcohol. This increases the average degree of oligomerization of the lauryloligoglucoside formed from 2.2 to 5.

(2) In continuous operation, the material streams remain practically the same when changing the average degree of oligomerization.

(3) In preparing alkyloligoglycosides with high average degrees of oligomerization, the reaction mixtures remain readily stirrable.

(4) In the preparation of alkyloligoglycosides with low average degrees of oligomerization, relatively little alcohol needs to be used.

(5) The acid concentration can be adjusted very easily. The average degree of oligomerization of practical interest is in the range up to 15 and can be effectively controlled by the acid concentration.

The alkyloligoglycosides prepared by the present process are suitable as surfactants, lubricants, dye adjuvants, nontoxic food emulsifiers, humectants, or as polyols for producing polyurethanes.

Other features of the invention will become apparent in the course of the following descriptions of exemplary embodiments which are given for illustration of the invention and are not intended to be limiting thereof.

EXAMPLES

The average degree of oligomerization N (the average number of monosaccharide units per molecule) is determined by the following procedure:

10 g of purified alkyloligoglycoside is heated with 100 g of ethylene glycol and 5 ml of 20% sulfuric acid with stirring for 5 hours at 110° C. The mixture is then diluted with 100 ml of water, and the alcohol formed by glycolysis is extracted twice with 50 ml of hexane. The amount of alcohol A obtained from the combined extracts is determined by gas chromatography. The amount of carbohydrate K (amount of anhydrosaccharide) is then calculated from the following equation.

$$K = 10 - A \text{ (g)}$$

The average degree of oligomerization N can be calculated from the formula below with sufficient accuracy from the quantitative composition of the alkyloligoglycoside which is then known, and the molecular weights of the components:

$$N = \frac{K/M_K}{A/M_A}$$

In this equation, $M_K$ is the average molecular weight of the basic saccharride units and $M_A$ is the average molecular weight of the alcohol used.

EXAMPLE 1

100 g of n-butylglucoside is dissolved in 250 g of lauryl alcohol at 100° C. with stirring and is treated with 1.6 ml of 2 N sulfuric acid in butanol. The mixture is heated in a distillation apparatus and is kept for 1 hour at 10 mbar and 130° C., with n-butanol being distilled off. The mixture is cooled to 100° C., neutralized at normal pressure with 1.6 ml of 2 N sodium hydroxide solution, buffered with 0.1 g of sodium bicarbonate, and then stirred for 15 minutes longer. Readily volatile components are distilled off under aspirator vacuum. The mixture is then filtered, and the excess lauryl alcohol is distilled off under oil vacuum.

A pasty lauryloligoglucoside is obtained with an average degree of oligomerization N=2.2 glucose units.

Examples 2 to 9

The procedure of Example 1 is repeated. The amounts added in each case to 100 g of n-butylglycoside and the average degrees of oligomerization N of the products are tabulated in Table 1.

TABLE 1

| Example | Alcohol g | 2N $H_2SO_4$ ml | 2N NaOH ml | Degree of oligomerization N |
|---|---|---|---|---|
| 1 | 250 g Lauryl alcohol | 1.6 | 1.6 | 2.2 |
| 2 | 250 g Lauryl alcohol | 2.5 | 2.5 | 2.7 |
| 3 | 250 g Lauryl alcohol | 5.0 | 5.0 | 4.2 |
| 4 | 250 g Lauryl alcohol | 10.0 | 10.0 | 5.0 |
| 5 | 250 g Ziegler alcohol(1) | 1.6 | 1.6 | 3.9 |
| 6 | 250 g Ziegler alcohol(1) | 10.0 | 10.0 | 7.0 |
| 7 | 500 g Lauryl alcohol | 10.0 | 10.0 | 1.8 |
| 8 | 500 g Lauryl alcohol | 20.0 | 20.0 | 3.2 |
| 9 | 500 g Lauryl alcohol | 40.0 | 40.0 | 3.7 |

(1) Mixture of approxately 1% decanol, 72% dodecanol, 25% tetradecanol, and 1% hexadecanol, ALFOL ®1214 from Condea, D-2212 Brunsbuttel Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the preparation of alkyloligoglycosides, comprising the steps of:

contacting an alkylglycoside, an alkyloligoglycoside or mixture thereof, wherein said alkyl comprises 2–6 carbon atoms, with a $C_{4-24}$ alcohol in the presence of an acid catalyst, the molar ratio of said alcohol to said alkylglycoside or alkyloligoglycoside being from 10:1 to 0.5:1, wherein said alcohol has at least three carbon atoms more than the alkyl groups of said alkylglycoside or alkyloligoglycoside; and regulating the degree of oligomerization of said alkyloligoglycoside by adjusting the acid catalyst concentration, wherein increasing the acid catalyst concentration increases the degree of oligomerization.

2. The process of claim 1, wherein said effective acid concentration is 2–200 milliequivalents of said acid per kilogram of said alcohol.

3. The process of claim 1, wherein said acid is sulfuric acid.

4. The process of claim 1, wherein said alcohol has from 8–20 carbon atoms.

5. The process of claim 4, wherein said alkylglycosides and alkyloligoglycosides are butylglycosides and butyloligoglycosides or mixtures thereof.

6. The process of claim 5, wherein said butylglycosides and butyloligoglycosides are butylglucosides and butyloligoglucosides.

7. The process of claim 1, wherein 0.5–10 moles of said alcohol are used per mole of saccharide unit.

8. The process of claim 7, wherein 1–5 moles of said alcohol are used per mole of saccharide unit.

* * * * *